US012767554B2

(12) United States Patent
Moriya et al.

(10) Patent No.: US 12,767,554 B2
(45) Date of Patent: Oct. 20, 2026

(54) X-RAY SHIELDING MATERIAL, X-RAY INSPECTION APPARATUS INCLUDING SAME, AND METHOD OF MANUFACTURING X-RAY SHIELDING MATERIAL

(71) Applicant: ANRITSU CORPORATION, Kanagawa (JP)

(72) Inventors: Jyunichi Moriya, Kanagawa (JP); Naoya Saito, Kanagawa (JP)

(73) Assignee: ANRITSU CORPORATION, Kanagawa (JP)

( * ) Notice: Subject to any disclaimer, the term of this patent is extended or adjusted under 35 U.S.C. 154(b) by 0 days.

(21) Appl. No.: 18/800,596

(22) Filed: Aug. 12, 2024

(65) Prior Publication Data

US 2025/0074787 A1 Mar. 6, 2025

(30) Foreign Application Priority Data

Aug. 28, 2023 (JP) ................................ 2023-138237

(51) Int. Cl.
*C01G 41/00* (2006.01)
*A61B 6/10* (2006.01)

(52) U.S. Cl.
CPC .............. *C01G 41/006* (2013.01); *A61B 6/10* (2013.01); *C01P 2006/32* (2013.01)

(58) Field of Classification Search
CPC ...... C01G 41/006; C01P 2006/32; A61B 6/10
USPC .......................................................... 252/515
See application file for complete search history.

(56) References Cited

U.S. PATENT DOCUMENTS

2005/0188790 A1 9/2005 Amick
2021/0170681 A1 * 6/2021 Wang .................... B29C 64/364

FOREIGN PATENT DOCUMENTS

| | | | | |
|---|---|---|---|---|
| JP | 2002-025792 | A | | 1/2002 |
| JP | 3362725 | B2 | * | 1/2003 |
| JP | 2004069385 | A | * | 3/2004 |
| JP | 2016109622 | A | * | 6/2016 |
| JP | 2018200261 | A | | 12/2018 |
| JP | 2020051799 | A | | 4/2020 |

OTHER PUBLICATIONS

Cione "The Shielding Against Radiation Produced by Powder Metallurgy With Tungsten Copper Alloy Applied on Transport Equipment for Radio-Pharmaceutical Products." 2015 International Nuclear Atlantic Conference—INAC 2015 (Year: 2015).*
Translation of JP2016109622A (Year: 2016).*
Translation of JP3362825B2 (Year: 2003).*
Translation of JP_2004069385-A (Year: 2004).*

* cited by examiner

*Primary Examiner* — Tri V Nguyen
(74) *Attorney, Agent, or Firm* — McDonald Hopkins LLC

(57) ABSTRACT

Provided are an X-ray shielding material capable of improving heat dissipation efficiency as compared with the related art, and thus contributing to reduction in size and manufacturing cost of an X-ray inspection apparatus, an X-ray inspection apparatus including the X-ray shielding material, and a method of manufacturing an X-ray shielding material. The X-ray shielding material is used in an X-ray inspection apparatus and shields X-rays, and the X-ray shielding material is configured by a sintered body containing a metal binder formed of metal having a higher thermal conductivity than lead, and a metal powder of metal having predetermined shielding performance against the X-rays.

5 Claims, 4 Drawing Sheets

X-RAY SHIELDING MATERIAL, X-RAY INSPECTION APPARATUS INCLUDING SAME, AND METHOD OF MANUFACTURING X-RAY SHIELDING MATERIAL

TECHNICAL FIELD

The present invention relates to an X-ray shielding material, an X-ray inspection apparatus, and a method of manufacturing an X-ray shielding material.

BACKGROUND ART

An X-ray inspection apparatus includes an apparatus that generates heat, such as an X-ray generation device and a computation device, and thus is likely to increase in temperature. On the other hand, the X-ray inspection apparatus is provided with a shielding member that shields unnecessary X-rays in order to prevent leakage of X-rays, and lead is often used as the shielding member.

However, since lead has a low thermal conductivity, it is difficult to dissipate heat from the shielding member using lead. Therefore, a cooling unit such as a heat dissipation device or an air conditioner is mounted on the X-ray inspection apparatus.

For example, Patent Document 1 discloses an X-ray generation device in which an electric fan that causes insulating oil to flow by convection is provided in a tube container, several fins for heat dissipation is provided on an outer surface of the tube container, and a fan that air-cools the fins is further provided, so that it is possible to dissipate heat generated in an X-ray tube to the outside with high efficiency and a simple configuration.

RELATED ART DOCUMENT

Patent Document

[Patent Document 1] JP-A-2002-25792

DISCLOSURE OF THE INVENTION

Problem that the Invention is to Solve

However, in the X-ray generation device or the X-ray inspection apparatus including the cooling unit as disclosed in Patent Document 1, the device is enlarged or the manufacturing cost is increased due to the installation of the cooling unit.

The present invention has been made in view of the above-described circumstances, and an object of the present invention is to provide an X-ray shielding material capable of improving a heat dissipation efficiency as compared with the related art, and thus contributing to reduction in size and manufacturing cost of an X-ray inspection apparatus, an X-ray inspection apparatus including the X-ray shielding material, and a method of manufacturing the X-ray shielding material.

Means for Solving the Problem

An X-ray shielding material according to a first aspect of the present invention is used in an apparatus using X-rays and shields X-rays. The X-ray shielding material is configured by a sintered body containing a metal binder formed of metal having a higher thermal conductivity than lead, and a metal powder of metal having predetermined shielding performance against the X-rays.

With this configuration, since the X-ray shielding material according to the present invention is configured by the sintered body containing the metal binder formed of metal having a higher thermal conductivity than lead and the metal powder of the metal having predetermined shielding performance against X-rays, it is possible to improve heat dissipation efficiency as compared with a conventional X-ray shielding material formed of only lead, for example. Therefore, in the X-ray inspection apparatus using the X-ray shielding material according to the present invention, it is possible to omit or simplify the cooling unit. Thus, the X-ray shielding material according to the present invention can contribute to reduction in size and manufacturing cost of the X-ray inspection apparatus.

In an X-ray shielding material according to a second aspect of the present invention, in the X-ray shielding material according to the first aspect, preferably, the metal binder is formed of at least one or more kinds of metal having a higher thermal conductivity than lead among kinds of metal having an atomic number of 13 or larger, and the metal powder is formed of at least one or more kinds of metal having an atomic number of 56 or larger.

With this configuration, in the X-ray shielding material according to the present invention, since the metal binder is formed of at least one or more kinds of metal having a higher thermal conductivity than lead among kinds of metal having an atomic number of 13 or larger, and the metal powder is formed of at least one or more kinds of metal having an atomic number of 56 or larger, it is possible to use the metal having a higher thermal conductivity than lead as the metal binder, and use the metal having a large specific gravity as the metal powder.

In an X-ray shielding material according to a third aspect of the present invention, in the X-ray shielding material according to the first aspect, preferably, the metal binder is configured by any one of silver, copper, and aluminum, and the metal powder is configured by tungsten.

With this configuration, in the X-ray shielding material according to the present invention, since the metal binder is configured by any one of silver, copper, and aluminum, and the metal powder is configured by tungsten, it is possible to be harmless to the human body and further improve the heat dissipation efficiency while maintaining the suitable shielding performance.

An X-ray inspection apparatus according to a fourth aspect of the present invention includes an X-ray generator that generates X-rays, an X-ray detector that detects the X-rays, and a shielding member that shields the X-rays, and has a configuration in which the X-ray shielding material according to the first aspect is used as the shielding member. In addition, an X-ray inspection apparatus according to a fifth aspect of the present invention includes an X-ray generator that generates X-rays, an X-ray detector that detects the X-rays, and a shielding member that shields the X-rays, and has a configuration in which the X-ray shielding material according to the second aspect is used as the shielding member. In addition, an X-ray inspection apparatus according to a sixth aspect of the present invention includes an X-ray generator that generates X-rays, an X-ray detector that detects the X-rays, and a shielding member that shields the X-rays, and has a configuration in which the X-ray shielding material according to the third aspect is used as the shielding member.

With this configuration, in the X-ray inspection apparatus in the fourth to sixth aspects of the present invention, since the X-ray shielding material according to any one of the first to third aspects is used as the shielding member that shields the X-rays generated by the X-ray generator, it is possible to also apply the X-ray shielding material that is lightweight while maintaining the shielding performance of the X-rays to the shielding member that has a complicated shape and is used in the X-ray inspection apparatus.

In an X-ray inspection apparatus according to a seventh aspect of the present invention, in the X-ray inspection apparatus according to the fourth aspect, a box that accommodates the X-ray generator and/or a housing in which the box is accommodated is formed by the shielding member. With this configuration, it is possible to realize an X-ray inspection apparatus that is lightweight while maintaining the shielding performance of the X-rays.

In an X-ray inspection apparatus according to an eighth aspect of the present invention, in the X-ray inspection apparatus according to the fourth aspect, the shielding member is disposed in a curtain shape on a transport path on which an inspection object is transported from a transport inlet to a transport outlet inside the apparatus. With this configuration, it is possible to reliably prevent leakage of X-rays to the outside of the apparatus.

A method of manufacturing an X-ray shielding material according to a ninth aspect of the present invention is a method of manufacturing an X-ray shielding material that shields X-rays and includes a sintering step of obtaining a sintered body by using metal having a higher thermal conductivity than lead as a metal binder and sintering a metal powder of metal having predetermined shielding performance against X-rays.

According to the method of manufacturing an X-ray shielding material in the ninth aspect of the present invention, it is possible to manufacture an X-ray shielding material in which the heat dissipation efficiency is improved as compared with a conventional X-ray shielding material formed of only lead, for example.

In a method of manufacturing an X-ray shielding material according to a tenth aspect of the present invention, in the method of manufacturing an X-ray shielding material according to the ninth aspect, preferably, at least one or more kinds of metal having a higher thermal conductivity than lead among kinds of metal having an atomic number of 13 or larger are used as the metal binder, and at least one or more kinds of metal having an atomic number of 56 or larger are used as the metal powder.

According to the method of manufacturing an X-ray shielding material in the tenth aspect of the present invention, it is possible to use the metal having a higher thermal conductivity than lead as the metal binder, and use the metal having a large specific gravity as the metal powder.

In a method of manufacturing an X-ray shielding material according to an eleventh aspect of the present invention, in the method of manufacturing an X-ray shielding material according to the ninth aspect, preferably, any one of silver, copper, and aluminum is used as the metal binder, and tungsten is used as the metal powder.

According to the method of manufacturing an X-ray shielding material according to the present invention, it is possible to manufacture an X-ray shielding material capable of being harmless to the human body and further improving the heat dissipation efficiency while maintaining suitable shielding performance.

Advantage of the Invention

According to the present invention, it is possible to provide an X-ray shielding material capable of improving heat dissipation efficiency as compared with the related art, and thus contributing to reduction in size and manufacturing cost of an X-ray inspection apparatus, an X-ray inspection apparatus including the X-ray shielding material, and a method of manufacturing the X-ray shielding material.

BEST MODE FOR CARRYING OUT THE INVENTION

Hereinafter, an X-ray shielding material according to an embodiment of the present invention and an X-ray inspection apparatus in which the X-ray shielding material is used will be described with reference to the drawings.

(X-Ray Inspection Apparatus)

Figure 1:
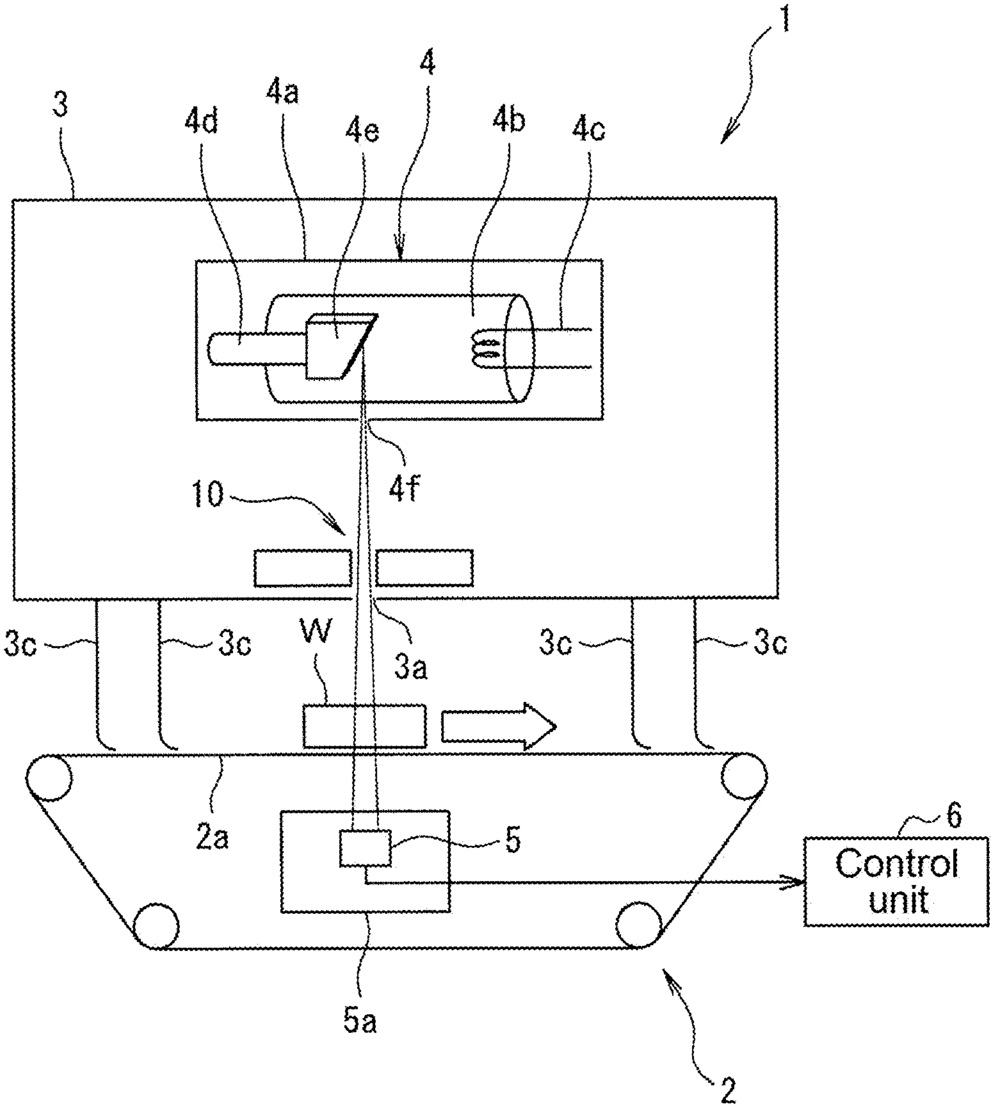
FIG. 1 is a schematic configuration view of an X-ray inspection apparatus including an X-ray shielding material according to an embodiment of the present invention.

As shown in FIG. 1, an X-ray inspection apparatus 1 in the present embodiment is incorporated into, for example, a part of a transport line, and irradiates an inspection object W that is transported sequentially from an upstream side with X-rays, performs various inspections such as whether or not foreign matters are contained, whether or not a defect has occurred in a seal portion, and whether or not there is a defective product based on an X-ray transmittance in which X-rays are transmitted through the inspection object W during this time, and then transports the inspection object W to a downstream side.

The X-ray inspection apparatus 1 in the present embodiment is an example of an X-ray inspection apparatus in which an X-ray shielding material according to the present invention is used, and is not limited thereto. That is, the X-ray shielding material according to the present invention can be generally applied to a wide variety of X-ray inspection apparatuses that are different depending on the irradiation method of X-rays or the type of inspection object.

As shown in FIG. 1, the X-ray inspection apparatus 1 in the present embodiment includes a transport unit 2, a housing 3, an X-ray generator 4, an X-ray detector 5, and a control unit 6.

The transport unit 2 is configured by, for example, a belt conveyor disposed horizontally with respect to the apparatus body, and transports an inspection object W as an inspection target on a transport path.

The transport unit 2 includes a transport belt **2*a* configured by a material (an element other than an element having a large atomic weight) through which X-rays are easily transmitted. When an inspection object W is inspected, the transport unit 2 drives the transport belt 2*a*** at a transport speed set in advance by the rotation of a drive motor based on control of a transport control unit (not shown). As a result, the inspection object W that has been transported from the transport inlet is transported toward a transport outlet side in a transport direction (direction indicated by the arrow).

The housing 3 accommodates a unit on the X-ray irradiation side, which is provided on the upper portion side of the transport path of the inspection object W inside, and specifically accommodates the X-ray generator 4, a collimator 10, and the like inside.

An irradiation opening window 3*a* for performing irradiation with the X-rays from the X-ray generator 4 toward the X-ray detector 5 is formed on a bottom surface of the housing 3.

In the X-ray inspection apparatus 1 in the present embodiment, one or more strip-shaped shielding curtains 3*c* may be provided on the transport inlet side and the transport outlet side of the lower portion of the housing 3 as necessary to reliably prevent the leakage of the X-rays to the outside.

The X-ray generator 4 irradiates the inspection object W transported on the transport path in the transport direction from the transport inlet to the transport outlet with X-rays, and generates X-rays by causing electrons accelerated by applying a voltage to collide with a target.

The X-ray generator 4 has a configuration in which a cylindrical X-ray tube 4*b* provided inside a box 4*a* that is made of metal and forms a substantially rectangular parallelepiped shape is immersed in an insulating oil.

In the X-ray tube 4*b*, a cathode 4*c* and an anode target 4*e* supported by a support 4*d* are disposed to face each other at a predetermined distance, and X-rays are generated by irradiating the anode target 4*e* with an electron beam from the cathode 4*c*.

Irradiation with the X-rays generated by the anode target 4*e* as the X-ray source is performed from an emission window 4*f* toward the X-ray detector 5 through the collimator 10 in a screen shape.

The X-ray detector 5 is provided in a housing 5*a* that is provided on a lower portion side of the transport surface of the inspection object W to face the housing 3 at a predetermined distance in a height direction.

The X-ray detector 5 includes a photodiode (not illustrated) and a plurality of X-ray detection elements (not illustrated) each including a scintillator provided on the photodiode. As the X-ray detector 5, for example, an area sensor in which X-ray detection elements are disposed in a planar shape to be arranged in the transport direction and a direction perpendicular to the transport direction, or a line sensor in which X-ray detection elements are arranged in a line shape in the direction perpendicular to the transport direction can be used.

The X-ray detector 5 converts the X-rays which are transmitted through the inspection object W after being applied to the inspection object W from the X-ray generator 4, into an optical signal by a scintillator, and converts the optical signal into an electric signal by a photodiode to output the electric signal as X-ray transmission data.

The control unit 6 stores the X-ray transmission data input from the X-ray detector 5, and performs various inspections on the inspection object W based on the X-ray transmission data, for example, inspections of whether or not foreign matters are contained, whether or not a defect has occurred in a seal portion, and whether or not there is a defective product.

A touch panel type display device (not shown) in which, for example, a display unit and a setting operation unit are integrated is connected to the control unit 6. Various types of information such as an inspection result of the inspection object W and setting information are displayed on the touch panel type display device.

(X-Ray Shielding Material)

In the X-ray inspection apparatus 1 in the present embodiment, in order to prevent the leakage of X-rays in an amount exceeding a leakage reference amount, a shielding member that shields X-rays is used for each unit or a portion of each unit constituting the X-ray inspection apparatus 1.

For example, the shielding member is used for a member constituting the box 4*a* of the X-ray generator 4, a member constituting the housing 3, and the like. In addition, the shielding member may be lined on an inner side of the box 4*a* or the housing 3.

Figure 2:
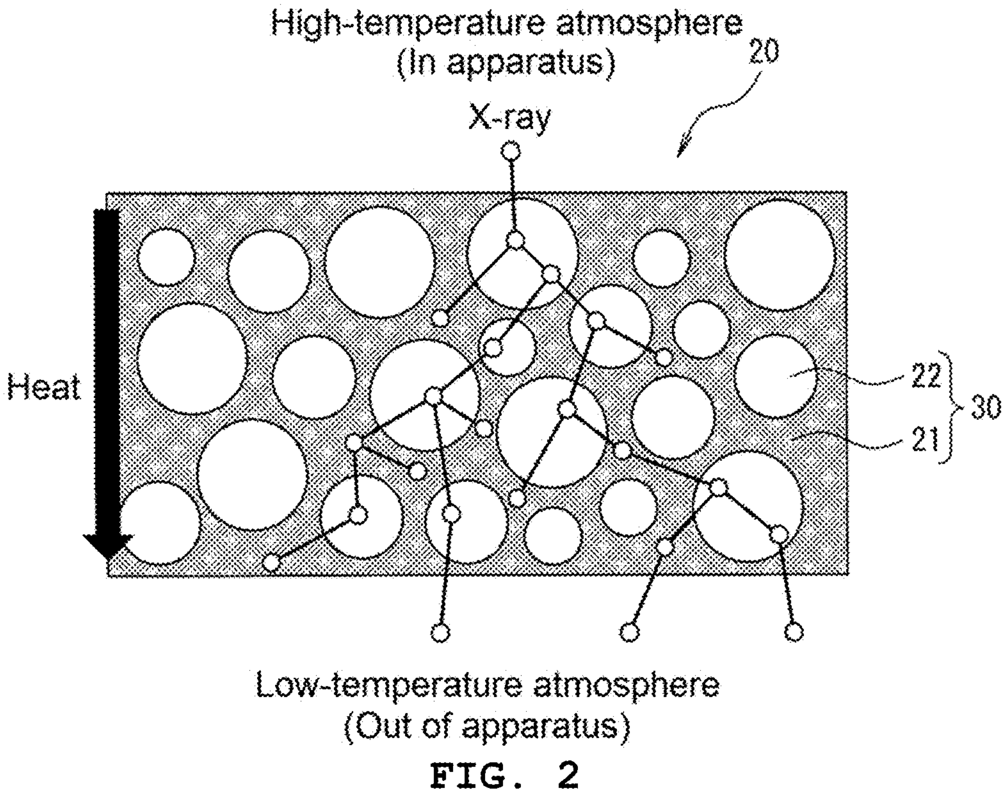
FIG. 2 is a cross-sectional view of the X-ray shielding material according to the embodiment of the present invention.

In the X-ray inspection apparatus 1 in the present embodiment, as the shielding member described above, an X-ray shielding material 20 as shown in FIG. 2 is used. FIG. 2 shows a cross section of a plate member in a direction perpendicular to a plane of the plate member (for example, a surface facing the X-ray tube 4*b*) when the X-ray shielding material 20 is used for the plate member constituting the box 4*a* of the X-ray generator 4, for example.

As shown in FIG. 2, the X-ray shielding material 20 is configured by a sintered body 30 containing a metal binder 21 formed of metal having a higher thermal conductivity than lead, and a metal powder 22 formed of metal having predetermined shielding performance against X-rays generated by the X-ray generator 4. The predetermined shielding performance is, for example, shielding performance required to prevent the leakage of X-rays in an amount exceeding a leakage reference amount in the X-ray shielding material 20 having a predetermined dimension.

The sintered body 30 is produced by sintering the metal powder 22 using the metal binder 21 as a binder in a manufacturing method described below.

As the metal binder 21, metal having an atomic number of 13 or larger can be used. For example, any one of aluminum, titanium, iron, nickel, copper, zinc, silver, tin, barium, and bismuth can be used. Furthermore, in the present embodiment, it is preferable that the metal binder 21 is metal having a higher thermal conductivity than lead among kinds of metal having an atomic number of 13 or larger. More suitably, the metal binder 21 is formed of any one of silver, copper, and aluminum, and copper is most preferable. Copper is preferable as the metal binder 21 because copper is relatively inexpensive and can achieve a desired thermal conductivity.

The metal binder 21 may be configured by a compound containing metal having an atomic number of 13 or larger. In this case, the metal binder 21 is preferably configured by a compound containing aluminum, titanium, iron, nickel, copper, zinc, silver, tin, barium, and bismuth. Furthermore, it is more suitable that the metal forming the compound includes at least any one of silver, copper, and aluminum.

The metal powder 22 is preferably formed by metal having an atomic number of 56 or larger, and more suitably is formed by tungsten. The metal powder 22 may be configured by a compound containing metal having an atomic number of 56 or larger. In this case, tungsten is preferably contained as the metal forming the compound.

Since the X-ray shielding material 20 configured as described above is formed by sintering the metal powder 22 of tungsten having a high density and a high specific gravity using the metal binder 21 as a binder, X-rays incident on the X-ray shielding material 20 are attenuated or shielded by the tungsten metal powder 22, whereby the X-ray shielding material 20 prevents transmission of the X-rays. In addition, since the metal binder 21 forming the X-ray shielding material 20 is formed of any one of silver, copper, and aluminum, and the atomic number of the metal is smaller than that of the metal powder 22, it is possible to suppress secondary X-rays generated inside.

That is, the X-rays incident on the X-ray shielding material 20 are attenuated or shielded by tungsten remaining in the sintered body 30 as a powder, and furthermore, the secondary X-rays generated from the tungsten metal powder 22 are also attenuated or shielded by the other tungsten metal powder 22. In addition, the secondary X-rays generated inside the X-ray shielding material 20 are also reduced by the metal binder 21 formed of any one of silver, copper, and aluminum in the sintered body 30. As a result, the X-rays incident from one surface (upper surface in FIG. 2) of the X-ray shielding material 20 are sufficiently attenuated or shielded in a case of being transmitted through the inside of the X-ray shielding material 20, and energy is greatly attenuated in a case of being transmitted to the other surface (lower surface in FIG. 2) side of the X-ray shielding material 20.

As described above, the X-ray shielding material 20 in the present embodiment is formed by sintering the tungsten metal powder 22, but has the same extent of shielding performance as a shielding body formed of only metal having a large atomic number, such as tungsten. Further, the X-ray shielding material 20 in the present embodiment is lighter than the shielding body formed of only metal having a large atomic number, such as tungsten.

Furthermore, in the X-ray shielding material 20 in the present embodiment, since the metal having a higher thermal conductivity than lead is used as the metal binder 21, the heat in the apparatus, which is a high-temperature atmosphere, is rapidly transferred from one surface (upper surface in FIG. 2) side of the X-ray shielding material 20 to the outside of the apparatus, which is the other surface (lower surface in FIG. 2) side of the X-ray shielding material 20, via the metal binder 21 having a high thermal conductivity. As a result, the heat in the apparatus in the high-temperature atmosphere is efficiently dissipated to the outside of the apparatus by the metal binder 21.

(Method of Manufacturing X-ray Shielding Material)

Next, a method of manufacturing the X-ray shielding material 20 in the present embodiment will be described.

The X-ray shielding material 20 in the present embodiment is manufactured by the following steps including a sintering step of obtaining a sintered body 30 by using the metal having higher thermal conductivity than lead as the metal binder 21 and sintering the metal powder 22 of metal having predetermined shielding performance against X-rays generated by the X-ray generator 4.

<Mixing and Grinding Step>

First, the metal powder 22 and the metal binder 21, which are the main materials of the X-ray shielding material 20, are finely ground, or the metal powder 22 and the metal binder 21 are mixed with each other so that a desired proportion is obtained. In order to improve sinterability, a sintering aid may be added to the metal powder 22 and the metal binder 21 within a range that does not affect the material properties.

<Molding Step>

In a molding step, the metal powder 22 and the metal binder 21 mixed in the mixing and grinding step are put into a mold having a shape of a shielding member of the X-ray inspection apparatus 1, and are compressed and molded by a press machine. In this case, an organic substance such as wax may be added as a molding aid.

<Sintering Step>

In the sintering step, the molded body molded in the molding step is placed in a sintering furnace and heated at a temperature lower than the melting point of the metal powder 22 and the melting point of the metal binder 21 for a predetermined time to be baked and solidified. As a result, the metal powders are bonded to each other by the diffusion phenomenon, and the sintered body 30 is completed.

<Machining Processing Step>

The sintered body 30 obtained in the above-described sintering step may be subjected to machining processing such as pulverizing or polishing, or may be subjected to a heat treatment or the like for increasing the hardness, as necessary.

Actions and Effects

As described above, since the X-ray shielding material according to the present embodiment is configured by the sintered body 30 containing the metal binder 21 formed of metal having a higher thermal conductivity than lead and the metal powder 22 of the metal having predetermined shielding performance against X-rays generated by the X-ray generator 4, it is possible to improve heat dissipation efficiency as compared with a conventional X-ray shielding material formed of only lead, for example. Therefore, in the X-ray inspection apparatus 1 using the X-ray shielding material according to the present embodiment, it is possible to omit or simplify the cooling unit. Thus, the X-ray shielding material according to the present embodiment can contribute to reduction in size and manufacturing cost of the X-ray inspection apparatus 1.

In addition, in the X-ray shielding material according to the present embodiment, since the metal binder 21 is formed of at least one or more kinds of metal having a higher thermal conductivity than lead among kinds of metal having an atomic number of 13 or larger, and the metal powder 22 is formed of at least one or more kinds of metal having an atomic number of 56 or larger, it is possible to use the metal having a higher thermal conductivity than lead as the metal binder 21, and use the metal having a large specific gravity as the metal powder 22.

In addition, in the X-ray shielding material according to the present embodiment, since the metal binder 21 is configured by any one of silver, copper, and aluminum, and the metal powder 22 is configured by tungsten, it is possible to be harmless to the human body and further improve the heat dissipation efficiency while maintaining the suitable shielding performance.

In addition, in the X-ray inspection apparatus according to the present embodiment, since the X-ray shielding material 20 is used as the shielding member that shields the X-rays generated by the X-ray generator 4, it is possible to omit or simplify the cooling unit, and reduce the size and reduce the manufacturing cost.

In addition, according to the method of manufacturing an X-ray shielding material according to the present embodiment, it is possible to manufacture the X-ray shielding material 20 in which the heat dissipation efficiency is improved as compared with a conventional X-ray shielding material formed of only lead, for example.

First Modification Example

Figure 3:
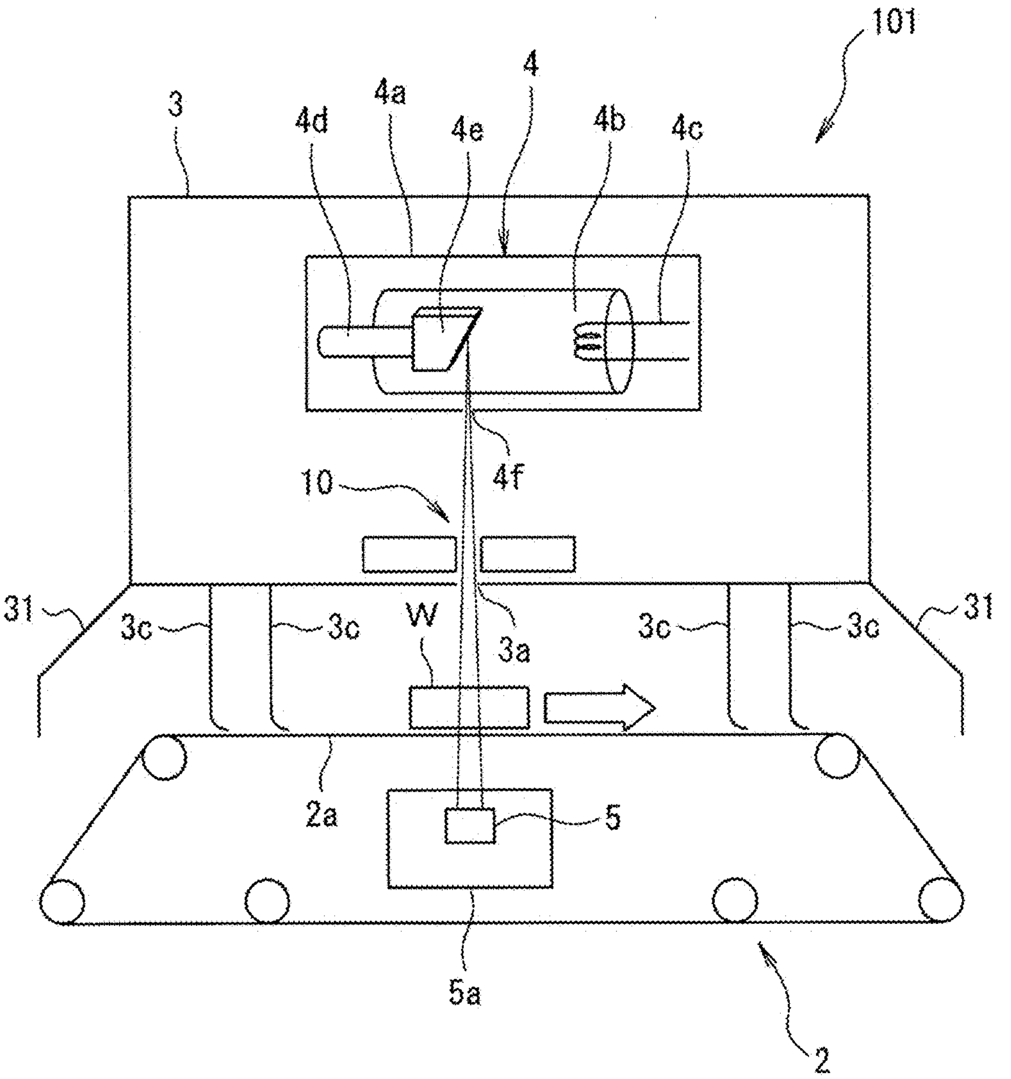
FIG. 3 is a view showing a first modification example of the X-ray inspection apparatus provided with the X-ray shielding material according to the embodiment of the present invention.

The X-ray shielding material according to the present invention may be used as a shielding member constituting a shielding cover 31 that is provided on the upper portion of a transport inlet and a transport outlet of an inspection object W in an X-ray inspection apparatus 101 according to a first modification example as shown in FIG. 3.

Second Modification Example

Figure 4:
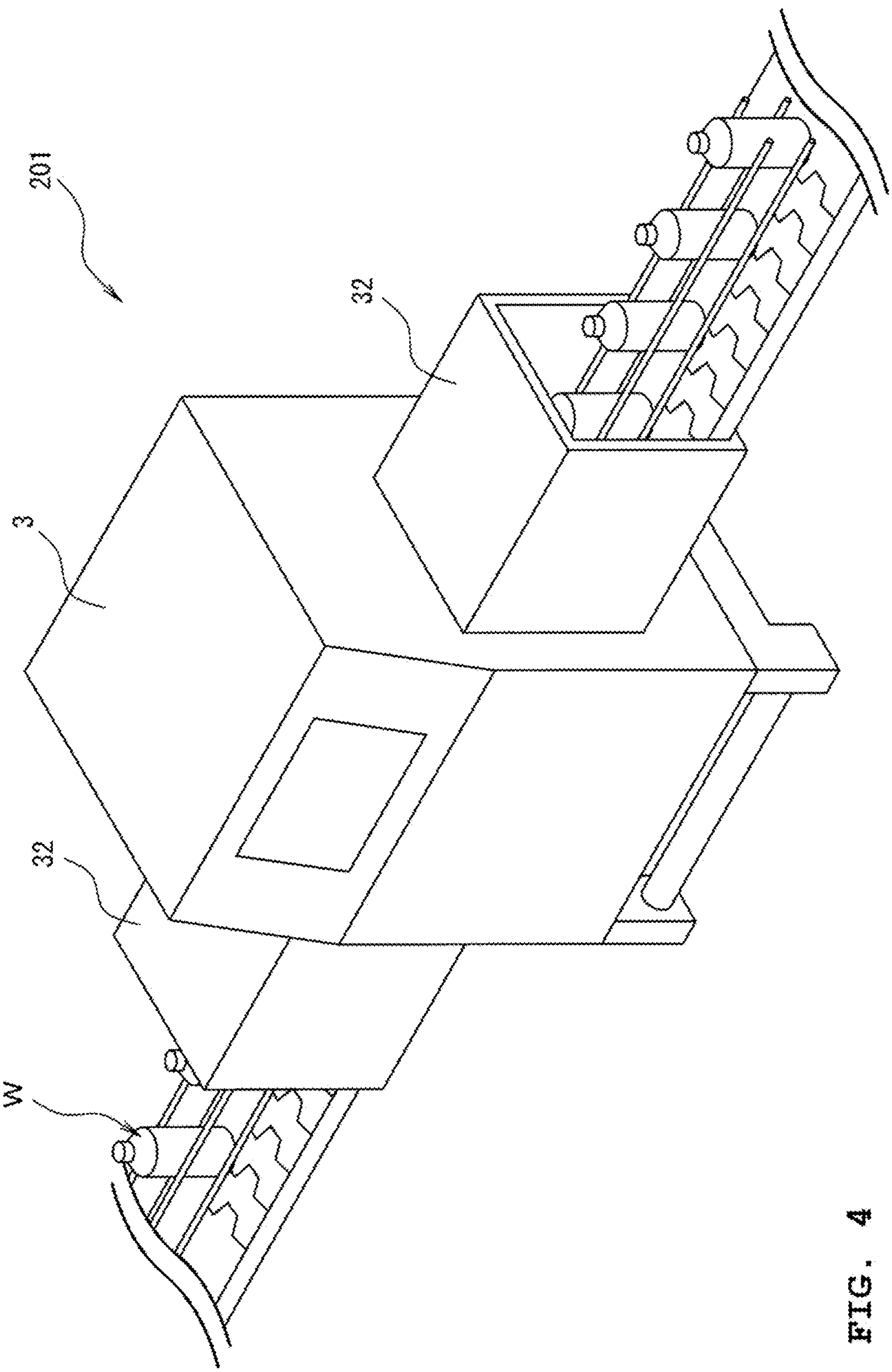
FIG. 4 is a view showing a second modification example of the X-ray inspection apparatus provided with the X-ray shielding material according to the embodiment of the present invention.

In addition, the X-ray shielding material according to the present invention may be used as a shielding member constituting a shielding cover 32 that covers a transport inlet and a transport outlet of an inspection object W in an X-ray inspection apparatus 201 according to a second modification example as shown in FIG. 4.

In addition, the X-ray shielding material according to the present invention can also be applied to a shielding member used in an X-ray inspection apparatus other than the X-ray inspection apparatuses shown in the present embodiment, the first modification example, and the second modification example. For example, the X-ray shielding material according to the present invention may be used as a plate shielding gate provided at a transport inlet and a transport outlet in an X-ray inspection apparatus, and may be applied to any shielding member as long as the shielding member is provided to prevent the leakage of X-rays.

Hitherto, the embodiments of the present invention have been disclosed, but it is clear that changes can be made by those skilled in the art without departing from the scope of the present invention. All such modifications and equivalents are intended to be included in the claims as follows.

DESCRIPTION OF REFERENCE NUMERALS AND SIGNS

1, 101, 201 X-ray Inspection Apparatus
2 Transport Unit
3 Housing
4 X-ray generator
4*a* Box
5 X-ray Detector
5*a* Housing
6 Control Unit
20 X-ray Shielding Material (Shielding Member)
21 Metal Binder
22 Metal Powder
30 Sintered Body
31, 32 Shielding Cover
W Inspection Object

What is claimed is:

1. An X-ray inspection apparatus comprising:
an X-ray generator that generates X-rays and heat;
an X-ray detector that detects the X-rays; and
a shielding member that shields the X-rays and dissipates the heat generated by the X-ray generator, the shielding member comprising an X-ray shielding material that is configured by a sintered body containing a metal binder formed of metal having a higher thermal conductivity than lead, and a metal powder of metal having predetermined shielding performance against the X-rays.

2. The X-ray shielding material according to claim 1, wherein:
the metal binder is formed of at least one or more kinds of metal having a higher thermal conductivity than lead among kinds of metal having an atomic number of 13 or larger, and
the metal powder is formed of at least one or more kinds of metal having an atomic number of 56 or larger.

3. The X-ray shielding material according to claim 1, wherein:
the metal binder is configured by any one of silver, copper, and aluminum, and
the metal powder is configured by tungsten.

4. The X-ray inspection apparatus according to claim 1, wherein a box that accommodates the X-ray generator and/or a housing in which the box is accommodated is formed by the shielding member for shielding the X-rays dissipating the heat generated by the X-ray generator.

5. The X-ray inspection apparatus according to claim 1, wherein one or more strip-shaped shielding curtains formed by the shielding member are disposed on a transport path on which an inspection object is transported from a transport inlet to a transport outlet inside the apparatus.

* * * * *